United States Patent
Thankaraj Salammal et al.

(10) Patent No.: US 9,699,976 B2
(45) Date of Patent: Jul. 11, 2017

(54) **DIRECT AND INDIRECT ORGANOGENESIS OF *JATROPHA***

(71) Applicant: TEMASEK LIFE SCIENCES LABORATORY LTD., Singapore (SG)

(72) Inventors: Maria Shibu Thankaraj Salammal, Singapore (SG); Srinivasan Ramachandran, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 199 days.

(21) Appl. No.: 14/442,559

(22) PCT Filed: Oct. 30, 2013

(86) PCT No.: PCT/SG2013/000468
§ 371 (c)(1),
(2) Date: May 13, 2015

(87) PCT Pub. No.: WO2014/077779
PCT Pub. Date: May 22, 2014

(65) Prior Publication Data
US 2016/0286748 A1    Oct. 6, 2016

Related U.S. Application Data

(60) Provisional application No. 61/727,319, filed on Nov. 16, 2012.

(51) Int. Cl.
*A01H 4/00*    (2006.01)
*A01N 65/00*    (2009.01)
(Continued)

(52) U.S. Cl.
CPC ............. *A01H 4/005* (2013.01); *A01H 1/00* (2013.01); *A01H 4/00* (2013.01); *A01H 4/008* (2013.01);
(Continued)

(58) Field of Classification Search
CPC ...... A01H 4/005; A01H 4/008; A01H 5/0825; A01H 1/00; A01H 4/00; C12N 15/8261;
(Continued)

(56) References Cited

U.S. PATENT DOCUMENTS

2008/0196121 A1* 8/2008 Murali .................. A01H 4/008
800/278
2010/0251421 A1* 9/2010 Johnson ................ A01H 4/008
800/279

FOREIGN PATENT DOCUMENTS

| CN | 1799340 A | 7/2006 |
|---|---|---|
| CN | 101138320 A | 3/2008 |

(Continued)

OTHER PUBLICATIONS http://www.biologydiscussion.com/plants/plant-tissue-culture/plant-tissue-culture-media-types-constituents-preparation-and-selection/10656, "Plant Tissue Culture Media: Types, Constituents, Preparation and Selection," Nandkishor Jha, downloaded Jan. 27, 2017.*

(Continued)

*Primary Examiner* — Anne Grunberg
(74) *Attorney, Agent, or Firm* — Rothwell, Figg, Ernst & Manbeck, P.C.

(57) ABSTRACT

The present invention relates in general to plant biotechnology. More particularly, the present invention relates to methods and media compositions for the efficient direct organogenesis and indirect organogenesis of *Jathropha* plants, such as *Jatropha curcas*.

12 Claims, 3 Drawing Sheets

(51) Int. Cl.
*A01N 65/08* (2009.01)
*A01H 1/00* (2006.01)
*C12N 15/82* (2006.01)
*A01H 5/08* (2006.01)

(52) U.S. Cl.
CPC ........... *A01H 5/0825* (2013.01); *A01N 65/00* (2013.01); *A01N 65/08* (2013.01); *C12N 15/8201* (2013.01); *C12N 15/8205* (2013.01); *A01N 2300/00* (2013.01)

(58) Field of Classification Search
CPC C12N 15/8205; C12N 15/8201; A01N 65/00; A01N 65/08; A01N 2300/00
USPC ......... 800/278, 279, 293, 294, 298; 435/430
See application file for complete search history.

(56) References Cited

FOREIGN PATENT DOCUMENTS

| CN | 102316719 A | 1/2012 |
|---|---|---|
| WO | 0057690 A2 | 10/2000 |
| WO | 2008/012832 A2 | 1/2008 |

OTHER PUBLICATIONS http://cdn.intechopen.com/pdfs-wm/40181.pdf, Abobkar Saad and Ahmed Elshahed, Recent Advances in Plant in vitro Culture, Chapter 2, "Plant Tissue Culture Media," 2012, Intech, pp. 30-40.*
Sujatha Mulpuri et al, Shoot Bud Proliferation from Axillary Nodes and Leaf Sections of Non-toxic *Jatropha curcas* L., Plant Growth Regulation (2005) 47:83-90.*
Khurana-Kaul et al, Direct Shoot Regeneration from Leaf Explants of *Jatropha curcas* in Response to Thidiazuron and High Copper Contents in the Medium, Biologia Plantarum 54(2):369-372, 2010.*
Garg et al., Imperial J. Pharmacognosy & Natural Products 1(1): Jun. 2011, "Plant Tissue Culture of *Jatropha curcas* L.: A Review", pp. 5-13, www.imperialpharmajournals.com.*
Sharma et al, Regeneration in *Jatropha curcas*: Factors Affecting the Efficiency of in vitro Regeneration, Industrial Crops and Products 34(2011) 943-951.*
Kumar and Reddy, Plant regeneration through the direct induction of shoot buds from petiole explants of *Jatropha curcas*: a biofuel plant, Annals of Applied Biology, (2010) 367-375.*
Liang, J.-W., "Establihsment of tissue culture system and transformation of *Jatropha curcas*," University of Science and Technology of China, a dissertation of master's degree, Oct. 10, 2011, 6 pages.
Lu, W., et al., "Induction of callus from *Jatropha curcas* and rapid propagation," Chin J Appl Environ Biol, 2003, 9 (2):127-130 (English Abstract).
Sujatha, M. and Mukta, N., "Morphogenesis and plant regeneration from tissue cultures of *Jatropha curcas*," Plant Cell Tissue and Organ Culture, 1996, 44:135-141.
Office Action issued in related Chinese application No. 201380065542.0 dated Feb. 23, 2016, 12 pages.
Kumar, N. et al., "Plant Regeneration Through the Direct Induction of Shoot Buds From Petiole Explants of *Jatropha curcas*: a Biofuel Plant," Annals of Applied Biology, (2010), pp. 367-375, copyright 2010 The Authors.
International Search Report mailed Jan. 7, 2014, PCT/SG2013/000468, Filed: Oct. 30, 2013, Applicant: Temasek Life Sciences Laboratory Limited, 4 pages.

* cited by examiner

DIRECT AND INDIRECT ORGANOGENESIS OF *JATROPHA*

CROSS-REFERENCE TO RELATED APPLICATIONS

The present application is a national stage filing under 35 U.S.C. §371 of PCT/SG2013/000468, filed on 30 Oct. 2013, and related to and claims priority to U.S. provisional patent application Ser. No. 61/727,319, filed 16 Nov. 2012. Each application is incorporated herein in its entirety.

BACKGROUND OF THE INVENTION

The present invention relates in general to plant biotechnology. More particularly, the present invention relates to methods and media compositions for the efficient direct organogenesis and indirect organogenesis of *Jatropha* plants, such as *Jatropha curcas*.

The publications and other materials used herein to illuminate the background of the invention or provide additional details respecting the practice, are incorporated by reference, and for convenience are respectively grouped in the Bibliography.

*Jatropha curcas* belongs to the family Euphorbiaceae. *Jatropha* is a large genus comprising over 170 species. The plant *Jatropha curcas* lately attracted particular attention as a tropical energy plant. The seeds are crushed and the resulting oil can be processed to produce a high-quality biodiesel that can be used in a standard diesel car. The plant may yield more than four times as much fuel per hectare as that of soybean and more than ten times that of maize. A hectare of *Jatropha* has been claimed to produce 1,892 liters of fuel (http://en.wikipedia.org/wiki/Jatropha_oil). *Jatropha curcas* primarily propagated through seeds, and significant variations in seed yield and oil content have been observed in plants raised through seeds (Kumar & Reddy 2010, Pant et al., 2006; Jha et al., 2007). Thus, the conventional propagation through seeds is not reliable and vegetative propagation by stem cuttings is inadequate to meet the demand (Heller, 1996; Openshaw, 2000).

In vitro regeneration techniques offer a powerful tool for germplasm conservation, mass multiplication of true to type plants and genetic transformation. Considerable efforts have been devoted in the past two decades to develop efficient regeneration of *Jatropha curcas* using different composition of media. These reports include organogenesis from hypocotyl (He et al., 2009; Sharma et al., 2011; Sahoo et al., 2011), Epicotyl (Wei et al., 2004), petiole (Kumar and Reddy, 2010a,b, Dubey et al., 2010, Kumar et al., 2011a), stem (Singh et al., 2010) and leaf explants (Sujatha and Mukta, 1996; Sujatha et al., 2005; Deore and Johnson, 2007; Kumar et al., 2010a,b; Kumar et al., 2011a), shoot tip and nodal explant (Rajore & Batra (2005); Sreenivasachar, 2007; Datta et al 2007), cotyledon disc (Li et al., 2008) and somatic embryogenesis (Jha et al. 2007). The systems developed in the previous studies suffer from lack of efficiency and reproducibility and require large quantities of explants as starting material.

It is desired to develop efficient regeneration systems from thin sections of explants of *Jatropha curacus*.

SUMMARY OF THE INVENTION

The present invention relates in general to plant biotechnology. More particularly, the present invention relates to methods and media compositions for the efficient direct organogenesis and indirect organogenesis of *Jathropha* plants, such as *Jatropha curcas*.

Thus, the present invention provides a method for producing plants via organogenesis from explants obtained from a *Jatropha* plant, such as *Jatropha curcas*. In accordance with the present invention, explants were obtained from healthy plants. In one embodiment, the healthy plants were propagated from cuttings and maintained in a green house. In another embodiment, the healthy plants were obtained from a field. In accordance with the present invention, the explants are obtained from thin sections of petiole, pedicle, peduncle and rachis explants.

In one aspect, the method is a method for the direct organogenesis of *Jatropha* plants. In accordance with this aspect, the method comprises: (a) culturing thin sections of the explants described herein on a solid shoot bud induction medium to induce the formation of shoot buds, (b) culturing the shoot buds on a solid shoot bud proliferation and development medium to proliferate and develop the shoot buds, (c) culturing a shoot bud clump derived from the developed shoot buds on a solid shoot elongation medium to elongate shoots, (d) culturing elongated shoots separated from the shoot bud clump on a solid shoot maturation medium to mature the shoots, and (e) dipping the mature shoots in a liquid growth regulator solution and transferring the dipped shoots to soil for growth of *Jatropha* plants.

In a second aspect embodiment, the method is a method for the indirect organogenesis of *Jatropha* plants. In accordance with this aspect, the method comprises (a) culturing thin sections of the explants described herein on a solid callus induction medium to induce organogenic callus tissue, (b) culturing the organogenic callus tissue on a solid shoot bud induction medium to induce the formation of shoot buds, (c) culturing the shoot buds on a solid shoot bud proliferation and development medium to proliferate and develop the shoot buds, (d) culturing a shoot bud clump derived from the developed shoot buds on a solid shoot elongation medium to elongate shoots, (e) culturing elongated shoots separated from the shoot bud clump on a solid shoot maturation medium to mature the shoots, and (f) dipping the mature shoots in a liquid growth regulator solution and transferring the dipped shoots to soil for growth of *Jatropha* plants.

In one embodiment the solid shoot bud induction medium comprises MS basal salts (Murashige and Skoog, 1962), B5 vitamins (Gamborg et al., 1968), plant hormones, silver thiosulfate (STS) and casein hydolysate. In one embodiment, the plant hormones are a mixture of an auxin and cytokinins. In another embodiment, the auxin is indole-3-butyric acid (IBA). In a further embodiment, the cytokinins are thidiazuron (TDZ) and 6-benzylaminopurine (BA). In one embodiment the medium contains a source of carbon, such as sucrose and a solidifying agent, such as agar. In another embodiment the culturing is done in a light/dark cycle.

In one embodiment, the solid shoot bud proliferation and development medium comprises MS basal salts, B5 vitamins, plant hormones, adenine sulfate ($AdSO_4$) and casein hydrolysate. In one embodiment, the plant hormones are a mixture of an auxin and cytokinins. In another embodiment, the auxin is indole-3-butyric acid (IBA). In a further embodiment, the cytokinins are TDZ, BA and zeatin (Zn). In one embodiment the medium contains a source of carbon, such as sucrose and a solidifying agent, such as agar. In another embodiment the culturing is done in a light/dark cycle.

In one embodiment, the solid shoot elongation medium comprises MS basal salts, B5 vitamins, plant hormones, adenine sulfate (AdSO$_4$) and casein hydrolysate. In one embodiment, the plant hormones are a mixture of gibberellic acid (GA$_3$) and cytokinins. In another embodiment, the cytokinins are BA and kinetin (Kn). In one embodiment the medium contains a source of carbon, such as sucrose and a solidifying agent, such as agar. In another embodiment the culturing is done in a light/dark cycle.

In one embodiment, the solid shoot maturation medium comprises MS basal salts, B5 vitamins, plant hormones, adenine sulfate (AdSO$_4$) and casein hydrolysate. In one embodiment, the plant hormones are a mixture of GA$_3$, an auxin and a cytokinin. In another embodiment, eth auxin is IBA. In a further embodiment, the cytokinin is Kn. In one embodiment the medium contains a source of carbon, such as sucrose and a solidifying agent, such as agar. In another embodiment the culturing is done in a light/dark cycle.

In one embodiment, the liquid growth regulator solution comprises MS basal salts, B5 vitamins and an auxin hormone. In one embodiment, the auxin is IBA. In another embodiment, the growth of *Jatropha* plants is done in a light/dark cycle.

In one embodiment, the solid callus induction medium comprises MS basal salts, B5 vitamins, plant hormones and proline. In one embodiment, the plant hormones are a mixture of auxins and cytokinins. In another embodiment, the auxins are 2,4-dichlorophenoxyacetic acid (2,4-D) and IBA. In a further embodiment, the cytokinins are TDZ and BA. In one embodiment the medium contains a source of carbon, such as sucrose and a solidifying agent, such as agar. In another embodiment the culturing is done in a light/dark cycle.

BRIEF DESCRIPTION OF THE FIGURES

FIG. 2a: Explants inoculated on shoot induction medium showing shoot primordial formation after 2 weeks. FIG. 2b: Cultures showing well developed shoot buds after 4 weeks. FIG. 2c: Micro shoots formation from shoot buds. FIG. 2d: Elongation of shoots. FIG. 2e: Maturation of shoots. FIG. 2f: Ex vitro rooting of elongated shoot.

FIG. 3a: Explants, such as petiole explants, inoculated on callus induction medium showing bulging within a week. FIG. 3b: Compact callus formation in shoot induction medium after 2 weeks. FIG. 3c: Shoot bud induction after 4 weeks. FIG. 3d: Micro shoots development from shoot buds. FIG. 3e: Maturation of shoots. FIG. 3f: Ex vitro rooting of shoot.

DETAILED DESCRIPTION OF THE INVENTION

The present invention relates in general to plant biotechnology. More particularly, the present invention relates to methods and media compositions for the efficient direct organogenesis and indirect organogenesis of *Jatropha* plants, such as *Jatropha curcas*.

Figure 1A:
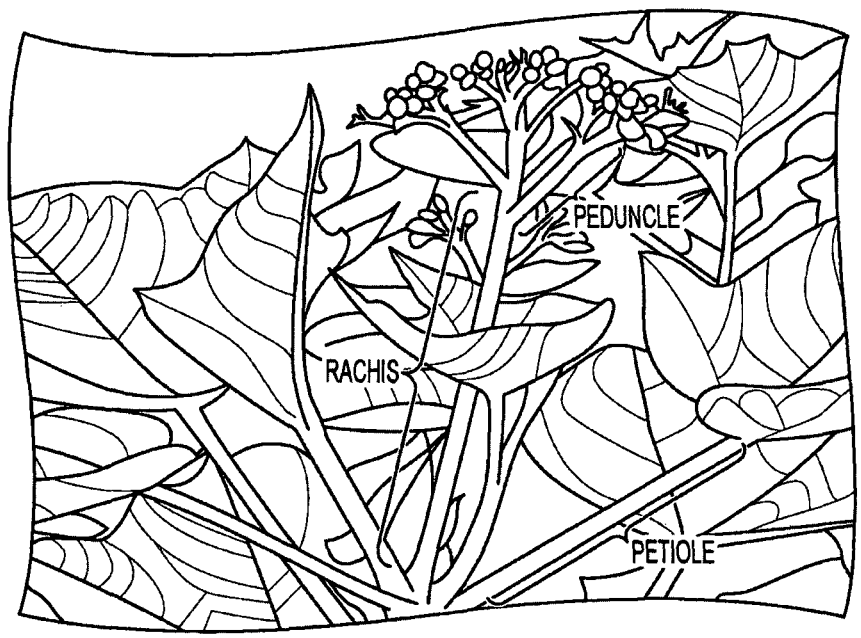
FIG. 1a shows a diagrammatic description of the sources for explants derived from petiole, peduncle and rachis tissues of *Jatropha curcas*.
Figure 1B:
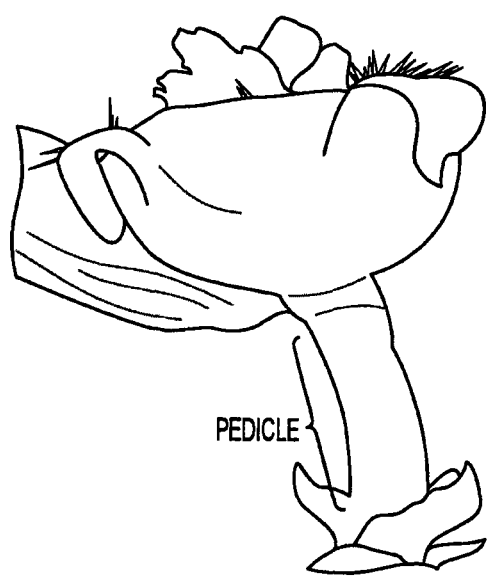
FIG. 1b shows a diagrammatic description of the source for explants derived from pedicle tissue of *Jatropha curcas*.
Figure 2A:
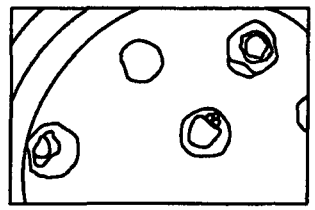
FIGS. 2a-f show representative stages of direct organogenesis from thin sections of explants (petiole, pedicle, peduncle, and rachis).
Figure 2B:
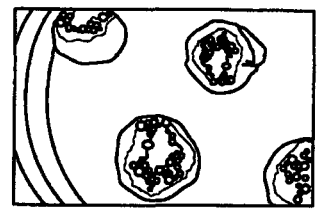
Figure 2C:
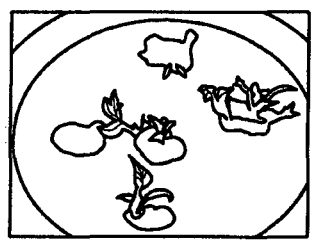
Figure 2D:
Figure 2E:
Figure 2F:
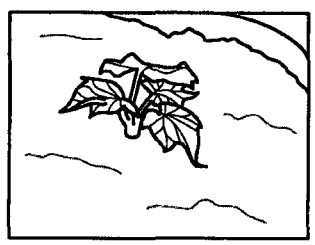
Figure 3A:
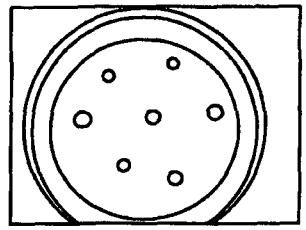
FIGS. 3a-f show representative stages of indirect organogenesis from thin sections of explants (petiole, pedicle, peduncle, and rachis).
Figure 3B:
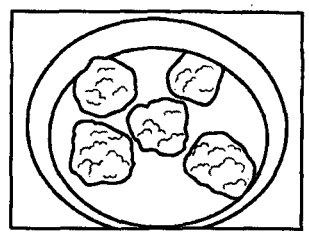
Figure 3C:
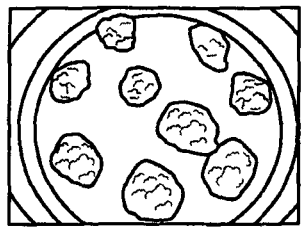
Figure 3D:
Figure 3E:
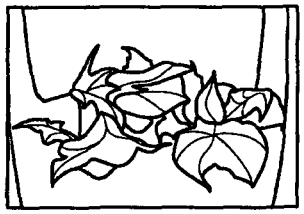
Figure 3F:
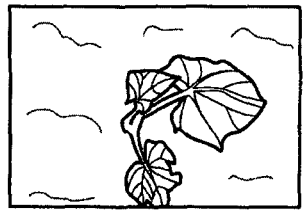

Thus, the present invention provides a method for producing plants via organogenesis from explants obtained from a *Jatropha* plant, such as *Jatropha curcas*. In accordance with the present invention, explants were obtained from healthy plants. In one embodiment, the healthy plants were propagated from cuttings and maintained in a green house. In another embodiment, the healthy plants were obtained from a field. In accordance with the present invention, the explants are obtained from thin sections of petiole, pedicle, peduncle and rachis explants (FIGS. 1a and 1b). In one embodiment, the explant is the petiole from the $2^{nd}$ to the $4^{th}$ leaf. In another embodiment, the explant is the pedicle, peduncle and rachis from the inflorescence before the onset of flowering. In one embodiment, the sections of explant are horizontally cut into thin sections of about 0.5 mm to about 1.0 mm thick, preferably <about 1.0 mm thick. In a further embodiment, the explants are washed in running tap water for about 3 min to about 7 min, preferably about 5 min. The explants are then washed in chlorohexidine surgical wash (two drops in 100 ml distilled water for about 8 min to about 12 min, preferably about 10 min to remove particles adhering on the surface. The explants are then surface sterilized in 0.1% HgCl$_2$ for about 8 min to about 12 min, preferably about 10 min followed by several, such as three, washes using sterilized distilled water.

In one aspect, the method is a method for the direct organogenesis of *Jatropha* plants. In accordance with this aspect, the method comprises: (a) culturing thin sections of the explants described herein on a solid shoot bud induction medium to induce the formation of shoot buds, (b) culturing the shoot buds on a solid shoot bud proliferation and development medium to proliferate and develop the shoot buds, (c) culturing a shoot bud clump derived from the developed shoot buds on a solid shoot elongation medium to elongate shoots, (d) culturing elongated shoots separated from the shoot bud clump on a solid shoot maturation medium to mature the shoots, and (e) dipping the mature shoots in a liquid growth regulator solution and transferring the dipped shoots to soil for growth of *Jatropha* plants.

In a second aspect embodiment, the method is a method for the indirect organogenesis of *Jatropha* plants. In accordance with this aspect, the method comprises (a) culturing thin sections of the explants described herein on a solid callus induction medium to induce organogenic callus tissue, (b) culturing the organogenic callus tissue on a solid shoot bud induction medium to induce the formation of shoot buds, (c) culturing the shoot buds on a solid shoot bud proliferation and development medium to proliferate and develop the shoot buds, (d) culturing a shoot bud clump derived from the developed shoot buds on a solid shoot elongation medium to elongate shoots, (e) culturing elongated shoots separated from the shoot bud clump on a solid shoot maturation medium to mature the shoots, and (f) dipping the mature shoots in a liquid growth regulator solution and transferring the dipped shoots to soil for growth of *Jatropha* plants.

In one embodiment the solid shoot bud induction medium comprises MS basal salts (Murashige and Skoog, 1962), B5 vitamins (Gamborg et al., 1968), plant hormones, silver thiosulfate (STS) and casein hydolysate. In one embodiment, the plant hormones are a mixture of an auxin and cytokinins. In another embodiment, the auxin is indole-3-butyric acid (IBA). In a further embodiment, the cytokinins are thidiazuron (TDZ) and 6-benzylaminopurine (BA). In one embodiment the medium contains about 0.05 µM to about 4.90 µM, preferably about 0.25 µM to about 3.67 µM, more preferably about 0.98 µM IBA. In another embodiment, the medium contains about 0.05 µM to about 2.27 µM, preferably about 0.09 µM to about 1.82 µM, more preferably about 0.45 µM TDZ. In a further embodiment, the medium contains about 0.02 µM to about 4.44 µM, preferably about 0.04 µM to about 3.33 µM, more preferably about 0.22 µM BA. In one embodiment, the medium contains about 0.10 µM to about 20.0 µM, preferably about 1.0 µM to about 10 µM, more preferably about 4.0 µM STS. In another embodiment, the medium contains about 5 mg/l to about 200 mg/l, preferably about 10 mg/l to about 150 mg/i, more preferably about 100 mg/l casein hydrolysate. In one embodiment the medium contains a source of carbon, such as sucrose and a solidifying agent, such as agar. Any suitable source of carbon and any suitable solidifying agent, each of which are well known to the skilled artisan can be used in this medium. In one embodiment, the sucrose is about 0.5% to about 10%, preferably about 1% to about 6%, more preferably about 3%. In another embodiment, the agar is about 0.5% to about 1.0%, preferably about 0.6% to about 0.9%, more preferably about 0.8%. In an additional embodiment, the culturing is done in a light/dark cycle. In a further embodiment, the light cycle is 16 hr light/8 hr dark photoperiod conditions at a light intensity of 150 µEm$^{-2}$s$^{-1}$. The culturing is done at 25±2° C.

In one embodiment, the solid shoot bud proliferation and development medium comprises MS basal salts, B5 vitamins, plant hormones, adenine sulfate (AdSO$_4$) and casein hydrolysate. In one embodiment, the plant hormones are a mixture of an auxin and cytokinins. In another embodiment, the auxin is IBA. In a further embodiment, the cytokinins are TDZ, BA and zeatin (Zn). In one embodiment the medium contains about 0.05 µM to about 4.90 µM, preferably about 0.10 µM to about 3.67 µM, more preferably about 0.49 µM IBA. In another embodiment, the medium contains about 0.01 µM to about 2.27 µM, preferably about 0.05 µM to about 1.82 µM, more preferably about 0.23 µM TDZ. In a further embodiment, the medium contains about 0.04 µM to about 4.44 µM, preferably about 0.08 µM to about 3.33 µM, more preferably about 0.44 µM BA. In an additional embodiment, the medium contains about 0.05 µM to about 4.56 µM, preferably about 0.23 µM to about 3.42 µM, more preferably about 0.92 µM Zn. In one embodiment, the medium contains about 5.43 µM to about 271.5 µM, preferably about 27.15 µM to about 162.9 µM, more preferably about 135.75 µM AdSO$_4$. In another embodiment, the medium contains about 5 mg/l to about 200 mg/l, preferably about 10 mg/l to about 150 mg/l, more preferably about 100 mg/l casein hydrolysate. In one embodiment the medium contains a source of carbon, such as sucrose and a solidifying agent, such as agar. Any suitable source of carbon and any suitable solidifying agent, each of which are well known to the skilled artisan can be used in this medium. In one embodiment, the sucrose is about 0.5% to about 10%, preferably about 1% to about 6%, more preferably about 3%. In another embodiment, the agar is about 0.5% to about 1.0%, preferably about 0.6% to about 0.9%, more preferably about 0.8%. In an additional embodiment, the culturing is done in a light/dark cycle. In a further embodiment, the light cycle is 16 hr light/8 hr dark photoperiod conditions at a light intensity of 150 µEm$^{-2}$s$^{-1}$. The culturing is done at 25±2° C.

In one embodiment, the solid shoot elongation medium comprises MS basal salts, B5 vitamins, plant hormones, adenine sulfate (AdSO$_4$) and casein hydrolysate. In one embodiment, the plant hormones are a mixture of gibberellic acid (GA$_3$) and cytokinins. In another embodiment, the cytokinins are BA and kinetin (Kn). In another embodiment, the medium contains about 0.03 µM to about 2.89 µM, preferably about 0.06 µM to about 2.17 µM, more preferably about 0.73 µM GA$_3$. In a further embodiment, the medium contains about 0.04 µM to about 4.44 µM, preferably about 0.08 µM to about 3.33 µM, more preferably about 0.66 µM BA. In an additional embodiment, the medium contains about 0.05 µM to about 4.65 µM, preferably about 0.23 µM to about 3.49 µM, more preferably about 1.17 µM Kn. In one embodiment, the medium contains about 5.43 µM to about 271.5 µM, preferably about 27.15 µM to about 162.9 µM, more preferably about 135.75 µM AdSO$_4$. In another embodiment, the medium contains about 5 mg/l to about 200 mg/l, preferably about 10 mg/l to about 150 mg/l, more preferably about 100 mg/l casein hydrolysate. In one embodiment the medium contains a source of carbon, such as sucrose and a solidifying agent, such as agar. Any suitable source of carbon and any suitable solidifying agent, each of which are well known to the skilled artisan can be used in this medium. In one embodiment, the sucrose is about 0.5% to about 10%, preferably about 1% to about 6%, more preferably about 3%. In another embodiment, the agar is about 0.5% to about 1.0%, preferably about 0.6% to about 0.9%, more preferably about 0.8%. In an additional embodiment the culturing is done in a light/dark cycle. In a further embodiment, the light cycle is 16 hr light/8 hr dark photoperiod conditions at a light intensity of 150 µEm$^{-2}$s$^{-1}$. The culturing is done at 25±2° C.

In one embodiment, the solid shoot maturation medium comprises MS basal salts, B5 vitamins, plant hormones, adenine sulfate (AdSo$_4$) and casein hydrolysate. In one embodiment, the plant hormones are a mixture of GA$_3$, an auxin and a cytokinin. In another embodiment, the auxin is IBA. In a further embodiment, the cytokinin is Kn. In another embodiment, the medium contains about 0.03 µM to about 2.89 µM, preferably about 0.06 µM to about 2.17 µM, more preferably about 0.73 µM GA$_3$. In a further embodiment, the medium contains about 0.05 µM to about 4.90 µM, preferably about 0.10 µM to about 3.67 µM, more preferably about 0.49 µM IBA. In an additional embodiment, the medium contains about 0.05 µM to about 4.65 µM, preferably about 0.47 µM to about 3.49 µM, more preferably about 1.17 µM Kn. In one embodiment, the medium contains about 5.43 µM to about 271.5 µM, preferably about 27.15 µM to about 162.9 µM, more preferably about 135.75 µM AdSO$_4$. In another embodiment, the medium contains about 5 mg/l to about 200 mg/l, preferably about 10 mg/l to about 150 mg/l, more preferably about 100 mg/l casein hydrolysate. In one embodiment the medium contains a source of carbon, such as sucrose and a solidifying agent, such as agar. Any suitable source of carbon and any suitable solidifying agent, each of which are well known to the skilled artisan can be used in this medium. In one embodiment, the sucrose is about 0.5% to about 10%, preferably about 1% to about 6%, more preferably about 3%. In another embodiment, the agar is about 0.5% to about 1.0%, preferably about 0.6% to about 0.9%, more preferably about 0.8%. In an additional embodiment, the culturing is done in a light/dark cycle. In a further embodiment, the light cycle is 16 hr light/8 hr dark photoperiod conditions at a light intensity of 150 µEm$^{-2}$s$^{-1}$. The culturing is done at 25±2° C.

In one embodiment, the liquid growth regulator solution comprises MS basal salts, B5 vitamins and an auxin hormone. In one embodiment, the auxin is IBA. In a further embodiment, the medium contains about 4.90 µM to about 245.0 µM, preferably about 9.8 µM to about 196.0 µM, more preferably about 49.0 µM IBA. In one embodiment, the bottoms of the shoots are washed using sterile distilled water to remove the traces of media prior to dipping in the liquid growth regulator solution. In another embodiment, the growth of *Jatropha* plants is done in a light/dark cycle. In one embodiment, the soil is potting soil or a potting mix. In another embodiment, well matured shoots started to produce new leaves and roots within 3 weeks of growth in the soil.

In one embodiment, the solid callus induction medium comprises MS basal salts, B5 vitamins, plant hormones and proline. In one embodiment, the plant hormones are a mixture of auxins and cytokinins. In another embodiment, the auxins are 2,4-dichlorophenoxyacetic acid (2,4-D) and IBA. In a further embodiment, the cytokinins are TDZ and BA. In another embodiment, the medium contains about 0.05 µM to about 4.53 µM, preferably about 0.09 µM to about 3.40 µM, more preferably about 0.45 µM 2,4-D. In a further embodiment, the medium contains about 0.05 µM to about 4.90 µM, preferably about 0.10 µM to about 2.45 µM, more preferably about 0.49 µM IBA. In an additional embodiment, the medium contains about 0.05 µM to about 2.27 µM, preferably about 0.09 µM to about 1.82 µM, more preferably about 0.45 µM TDZ. In one embodiment, the medium contains about 0.04 µM to about 4.44 µM, preferably about 0.08 µM to about 3.33 µM, more preferably about 0.66 µM BA. In another embodiment, the medium contains about 10 mg/l to about 500 mg/l, preferably about 25 mg/l to about 200 mg/l, more preferably about 100 mg/l proline. In one embodiment the medium contains a source of carbon, such as sucrose and a solidifying agent, such as agar. Any suitable source of carbon and any suitable solidifying agent, each of which are well known to the skilled artisan can be used in this medium. In one embodiment, the sucrose is about 0.5% to about 10%, preferably about 1% to about 6%, more preferably about 3%. In another embodiment, the agar is about 0.5% to about 1.0%, preferably about 0.6% to about 0.9%, more preferably about 0.8%. In an additional embodiment, the culturing is done in a light/dark cycle. In a further embodiment, the light cycle is 16 hr light/8 hr dark photoperiod conditions at a light intensity of 150 µEm$^{-2}$s$^{-1}$. The culturing is done at 25±2° C.

In the direct organogenesis method the following culturing times are used. Subculturing on fresh medium can be done about every 2-3 weeks, preferably about every 3 weeks, if necessary as would be well known to a skilled artisan.

Shoot bud induction: about 2 weeks to about 5 weeks, preferably about 4 weeks to about 5 weeks, more preferably about 4 weeks.

Shoot bud proliferation and development: about 2 weeks to about 4 weeks, preferably about 3 weeks to about 4 weeks, more preferably about 3 weeks.

Shoot elongation: about 2 weeks to about 4 weeks, preferably about 3 weeks to about 4 weeks, more preferably about 3 weeks.

Shoot maturation: about 2 weeks to about 6 weeks, preferably about 3 weeks to about 6 weeks, more preferably about 4 weeks. An additional same culture time could be used for those shoots that are not physiologically mature after the first culture period.

In the indirect organogenesis method the following culturing times are used. Sub culturing on fresh medium can be done every 3 weeks, if necessary as would be well known to a skilled artisan.

Callus induction: about 2 weeks to about 4 weeks, preferably about 2 weeks to about 3 weeks, more preferably about 3 weeks.

Shoot bud induction: about 4 weeks to about 8 weeks, preferably about 4 weeks to about 7 weeks, more preferably about 7 weeks. In a preferred embodiment, the callus is subcultured every two weeks on fresh medium.

Shoot bud proliferation and development: about 2 weeks to about 4 weeks, preferably about 3 weeks to about 4 weeks, more preferably about 3 weeks.

Shoot elongation: about 2 weeks to about 4 weeks, preferably about 3 weeks to about 4 weeks, more preferably about 3 weeks.

Shoot maturation: about 2 weeks to about 6 weeks, preferably about 3 weeks to about 6 weeks, more preferably about 4 weeks. An additional same culture time could be used for those shoots that are not physiologically mature after the first culture period.

In addition, the present invention provides systems which can be used for the transformation of plants of the genera *Jatropha*. The method of transformation/transfection is not critical to the transformation of plants of the genera *Jatropha*; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed. See, for example, Mathews et al. (1992), Neuhaus et al. (1987), Wilde et al. (1992), U.S. Pat. Nos. 7,241,937, 7,273,966 and 7,291,765 and U.S. Patent Application Publication Nos. 2007/0231905 and 2008/0010704. See also, International Published Application No. WO2005/103271.

In one embodiment, the explant tissue can be co-cultured with an *Agrobacterium* strain harboring a DNA constructs containing a gene or nucleic acid of interest using techniques well known in the art. Transformed tissue can be selected using conventional techniques well known in the art. In a further embodiment, the DNA can be introduced into the explant tissue using conventional techniques, such as particle bombardment. Transformed tissue can be selected using conventional techniques well known in the art. Transformed or transgenic plants can be regenerated using the organogenic methods described herein.

Similarly, the DNA that is inserted (the DNA of interest) into plants of the genera *Jatropha* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989; Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters is described in U.S. Pat. Nos. 6,506,962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The present invention shows the efficiency and use of thin sections of petiole, pedicle, peduncle and rachis explants for large scale in vitro production of *Jatropha curcas* plantlets for the first time. The methods employed direct and indirect shoot bud induction from thin sections of explants using medium containing MS basal salts and B5 vitamins supplemented with different concentrations of phytohormones and additives. The phytohormones include auxins, cytokinins and gibberellins. The additives include casein acid hydrolysate, proline, silver thiosulphate (STS). The highest efficiency (>90%) of shoot bud inductions were observed when explants and calli were placed on the medium containing TDZ, IBA, BA and STS. Medium containing different concentration of 2,4-D, TDZ, BA, IBA and proline were essential for induction of organogenic calli. The induced shoot buds were transferred to medium containing TDZ, BA, IBA, Zn, AdSO$_4$ and casein hydrolysate for shoot bud proliferation and development. The micro shoots could be elongated on MS medium containing different concentration of BA, Kn, AdSO$_4$, GA$_3$ and casein hydrolysate. The elongated shoots were cultured in medium containing different concentration of Kn, IBA, AdSO$_4$, GA$_3$ and casein hydrolysate to reach physiological maturity. The well matured shoots could me ex-vitro rooted by dipping in solution containing IBA, followed by transfer into the soil.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Green and Sambrook, 2012, *Molecular Cloning*, 4th Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke,

*RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods for Developing Cold-Adapted

Plant Material and Source of Explant:

*Jatropha curcas* hybrids were selected. Plants were propagated from cuttings and maintained in experimental green house of Temasek Lifesciences Laboratory, #1 Research link, National University of Singapore, Singapore 117604. These plants were used as source of explants.

Sterilization of Explant:

The petiole from 2nd to 4th leaf and pedicle, peduncle and rachis from inflorescence before the onset of flowering were selected as explant for the present study. Explants were initially washed in running tap water for 5 min and followed by wash in chlorohexidine surgical wash (two drops in 100 ml of distilled water) for 10 min to remove the adhering particles on the surface. The explants were surface sterilized in 0.1% $HgCl_2$ for 10 min followed by 3 washes using sterilized distilled water.

Culture Media and Conditions:

The chemicals used in the present study were purchased from Duchefa Biochemie, Haarlem, The Netherlands and Sigma Aldrich, Inc., St Louis, USA. The culture media composed of MS basal salts, B5 vitamins, 3% sucrose and 0.8% agar as solidifying agent. The pH of the media is adjusted to 5.6-5.8 before autoclaving. All the cultures were incubated at 25±2° C. with 16 hr light/8 hr dark photoperiod conditions at a light intensity of 150 $\mu Em^{-2}s^{-1}$. The culture conditions are same throughout the stages of organogenesis. The compositions of the culture media are shown in Table 1 which also shows the culture conditions for direct and indirect organogenesis from explants of *Jatropha curcas* in accordance with the present invention.

TABLE 1

Direct and Indirect Organogenesis from Thin Sections of Petiole, Pedicle, Peduncle and Rachis Explants of *Jatropha curcas* L.

| Stages | Media composition | Inference | | Period (Weeks) | |
|---|---|---|---|---|---|
| | | Direct | Indirect | Direct | Indirect |
| Callus induction | MS salts + B5 vitamin + 2,4-D (0.45 μM) + TDZ (0.45 μM), BA (0.66 μM) + IBA (0.49 μM) + proline (100 mg/l). | — | Callusing of explants from cut ends | — | 3 |
| Shoot bud induction | MS salts + B5 vitamin + TDZ (0.45 μM) + BA (0.22 μM) + IBA (0.98 μM) + STS (4.0 μM) + Casein hydrolysate (100 mg/l). | Initiation of buds from explants | Initiation of buds from calli | 4 | 7 |
| Shoot bud Proliferation and development | MS salts + B5 vitamin + TDZ (0.23 μM) + $AdSO_4$ (135.75 μM) + Zn (0.92 μM) + BA (0.44 μM), + IBA (0.49 μM) + Casein hydrolysate (100 mg/l). | Shoot bud proliferation and development | Shoot bud proliferation and development | 3 | 3 |
| Elongation | MS salts + B5 vitamin + BA (0.66 μM) + Kn (1.17 μM) + $AdSO_4$ (135.75 μM) + $GA_3$ (0.73 μM) + Casein hydrolysate (100 mg/l). | Elongation of shoots | Elongation of shoots | 3 | 3 |
| Maturation | MS salts + B5 vitamin + Kn (1.17 μM) + $AdSO_4$ (135.75 μM) + $GA_3$ (0.73 μM) + IBA (0.49 μM) + Casein hydrolysate (100 mg/l). | Shoots become strong and healthy | Shoots become strong and healthy | 4 | 4 |
| Ex-vitro Rooting | MS salts + B5 vitamin + IBA (49.0 μM) (Dipping Solution) | Rooting of shoots | Rooting of shoots | 3 | 3 |
| Total period taken to establish regeneration system from thin sections of petiole, pedicle, peduncle, rachis | | | | 17 | 23 |

Callus Induction:

The explants were horizontally cut into thin. (<1.0 mm thick) sections and cultured on callus induction medium containing 2,4-dichlorphenoxyacetic acid (2,4-D; 0.45 µM), thidiazuron (TDZ; 0.45 µM), 6-benzylaminopurine (BA; 0.66 µM), indole-3-butyric acid (IBA; 0.49 µM) and proline (100 mg/l).

Shoot Bud Induction:

The thin sections of all the explants (petiole, pedicle, peduncle and rachis) and the calli initiated from different explants (petiole, pedicle, peduncle and rachis) on callus induction medium were cultured on shoot induction medium containing TDZ (0.45 µM), BA (0.22 µM), IBA (0.98 µM), Silver thiosulfate (STS; 4.0 µM) and casein hydrolysate (100 mg/l).

Shoot Bud Proliferation and Development:

Shoot buds that were induced on the explant and calli were transferred to shoot bud proliferation and development medium containing TDZ (0.23 µM), adenine sulfate ($AdSO_4$; 135.75 µM), Zn (0.92 µM), BA (0.44 µM), Indole-3-butyric acid (IBA; 0.49 µM) and casein hydrolysate (100 mg/l).

Shoot Elongation:

Well developed shoot buds were dissected as shoot clump and were transferred to shoot elongation medium containing different concentrations of BA (0.66 µM), kinetin (Kn; 1.17 µM), $AdSO_4$ (135.75 µM), gibberellic acid ($GA_3$; 0.73 µM) and casein hydrolysate (100 mg/l).

Maturation of Shoots:

Elongated shoots were separated from the clump and cultured on the Maturation medium containing Kn (1.17 µM), $AdSO_4$ (135.75 µM), $GA_3$ (0.73 µM) IBA (0.49 µM) and casein hydrolysate (100 mg/l).

Ex Vitro Rooting:

Well matured shoots were selected and the bottoms were washed using sterile distilled water to remove the traces of media. Then the shoots were dipped in plant growth regulator solution containing different concentration of IBA (49.0 µM) and 0.5% Bavistin™ fungicide and transferred to a phyta tray containing autoclaved potting mix. MS salts+B5 vitamin+IBA (49.0 µM) (Dipping Solution).

Example 2

Organogenesis of *Jatropha curcas*

The present invention provides standardized methods for an efficient direct organogenesis system and an efficient indirect organogenesis system using thin section of petiole, pedicle, peduncle and rachis explants of *Jatropha curcas*. The direct organogenesis system proceeds directly shoot bud induction through shoot proliferation and development, shoot elongation, shoot maturation and rooting. The indirect organogenesis systems utilize a first callus induction step followed by the same stages as in the direct organogenesis system.

Callus Induction:

The explants inoculated on callus induction medium expanded and started producing green compact calli after one week of culture initiation. All the tested explants responded for callus induction with the efficiency of >95% and the induced calli were green compact and organogenic.

Shoot Bud Induction:

Thin sections of explants placed on shoot induction medium expanded and bended towards up and started to produce adventitious buds from the explants within 2 weeks. It was observed that the organogenic efficiency of thin sections comparatively decreases from distal end towards proximal end of the explant. Direct organogenesis was observed as induction of shoot buds directly from the explants without any intervening callus phase. The calli cultured on shoot induction medium become more compact after 2 weeks. The calli were sub-cultured in the same medium for every two weeks. Tiny shoots were observed on the calluses at the end of second subculture. The efficiency of shoot induction varied with explant and petiole explants were found to be best for direct organogenesis and showed a maximum response of >85% whereas rachis explant found to be best for indirect organogenesis and showed >90% response.

Shoot Proliferation and Development:

Shoot buds cultured on shoot proliferation and development media produced additional shoot buds and developed into micro shoots within three weeks. The shoot bud induced via direct organogenesis showed vigorous proliferation and less development whereas buds induced via indirect organogenesis showed less proliferation but much development.

Shoot Elongation:

The clumps containing micro shoots from the above steps when cultured on elongation medium started to elongate into shoots after 3 weeks. More than 50% of micro shoots were converted into shoots.

Maturation of Shoots:

Well elongated shoots were separated carefully from the clumps and transferred to maturation medium to induce physiological maturity. Most of the shoots culture in the maturation medium reached maturity within 3 weeks whereas some shoots still need additional 3 weeks and were cultured in the same medium to bring physiological maturity.

Direct Rooting:

Well matured shoots transferred in soil started to produce new leaves and roots within 3 weeks.

The present invention provides a simple, rapid and reproducible method for regenerating *Jatropha curcas* from petiole, pedicle, peduncle and rachis explants. These examples show the efficiency and use of thin sections of petiole, pedicle, peduncle and rachis explants for large scale production of tissue culture *Jatropha curcas* plantlets for the first time. Kumar et al. (2011b) obtained 57.61% response with petiole explant with an average 4.98 shoots per 0.5 cm length petiole explant in medium containing 2.27 µM TDZ, whereas in the present examples we obtained higher efficiency (>90%) with 7-10 shoots per explant. This result is in contrast to Kumar et al. (2011b) which teaches using high concentration of TDZ produced more abnormal buds and the further conversion of buds into shoots will be more difficult. Mishra et al. (2010) reported that, the shoot bud induction from leaf explant were visible within 4-6 weeks. In contrast, these examples show that by using our shoot induction medium it is possible to induce shoots within 2-3 weeks from all the explants tested. Singh et al. (2010) induced shoot buds from stem explants of *Jatropha curcas* in medium containing BA (4.44 µM) and Kn (4.65 µM). These examples show that only BA and Kn alone had no effect on shoot bud induction from the tested explants. Misra et al. (2010) used BA (2.22 µM) in combination with IBA (0.49 µM) for shoot bud induction from leaf explants. Culturing shoot buds on shoot bud proliferation and differentiation were found to be essential in the present invention for production of healthy shoot buds. In proliferation and development medium, TDZ concentration was reduced and $AdSO_4$ was added to enhance shoot bud proliferation and growth. Kumar and Reddy (2010) have reported that shoot buds cultured on MS medium containing BA, Kn and NAA induced shoot proliferation and subsequent transfer into MS medium containing BA and IAA for shoot elongation. This is in contrast to the observation in these examples that TDZ is essential for proliferation of shoot buds and Kn, AdSO$_4$, GA$_3$ in combination with BA are essential for elongation of healthy shoots. For efficient rooting the shoots must reach physiological maturity. In the present examples, we observed that the shoots reached maturity in medium containing Kn, GA$_3$ and IBA, presence of BA in maturation medium hindered maturation leading to abnormal shoot production and in vitro flowering. In the present examples, the tested explants (petiole, pedicle, peduncle and rachis) showed differences in the percentage of regeneration of shoot bud, number of shoot buds per explants. This result may be due to differences in the levels of endogenous hormones, particularly cytokinin levels during the regeneration period (Preece and Imel, 1991).

The present examples using petiole, peduncle, pedicle and rachis explant shows that thin sections of these explants are suitable for large scale production of *Jatropha curcas* tissue culture plantlets. Based on these examples by modifying the media compositions and adding additives, it is possible to regenerate more number of plants from thin sections of these explants. Though Sujatha and Dhingra (1993) reported shoot multiplication from peduncle explants of *Jatropha integerrima*, through literature survey it is very clear that this is the first report on in vitro regeneration from thin sections of petiole, pedicle, peduncle, rachis explants of *Jatropha curcas*. As shown by the present invention, approximately 7-10 healthy plants can be produced within a short span of 15-23 weeks from a thin section of explant. The present system is useful for large scale production of plantlets and genetic transformation.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Deore A C and Johnson T S (2008). High-frequency plant regeneration from leaf-disc cultures of *Jatropha curcas* L.: an important biodiesel plant. Plant Biotech Rep 2:10-15.

Dubey, A., Oreya, s., Gupta, N., Pandey, K L., Shah, P., Arif, M., 2010. In vitro regeneration of *Jatropha curcas* L. using petiole explants. Biochem. Cell. Arch. 10(1) 7-12.

Gamborg, O. L. et al. (1968). Nutrient requirements of suspension cultures of soybean root cells. *Exp Cell Res* 50:151-158.

He, Y., Guo, X., Lu, R., Niu, B., Pasapula, V., Hou, P., Cai, F., Xu, Y., Chen, F., (2009). Changes in morphology and biochemical indices in browning callus derived from *Jatropha curcas* hypocotyls. Plant Cell Tiss. Organ Cult. 98, 11-17.

Heller, J., 1996. Physic Nut, *Jatropha curcas*. Promoting the conservation and use of underutilized and neglected crops. Rome, Italy: International Plant Genetic Resources Institute (IPGRI).

Jha, T. B., Mukhejee, P., Datta, M. M., 2007. Somatic embryogenesis in *Jatropha curcas* Linn., an important biofuel plant. Plant Biotechnol. Rep. 1, 135-140.

Kumar N, and Reddy M P (2010). Plant regeneration through the direct induction of shoot buds from petiole explants of *Jatropha curcas*: a biofuel plant. Ann. Appl. Biol. 156: 367-375.

Kumar N, Vijay Anand K G, Reddy M P (2010a). A shoot regeneration from cotyledonary leaf explants of *Jatropha curcas*: a biodiesel plant. Acta Physiol. Plant. 32: 917-924.

Kumar, N., Vijay Anand, K. G., Pamidimarri, D. V. N. S., Sarkar, T., Reddy, M. P., Radhakrishnan, T., Kaul, T., Reddy, M. K., Sopori, S. K., (2010b). Stable genetic transformation of *Jatropha curcas* via *Agrobacterium tumefaciens*-mediated gene transfer using leaf explants. Ind. Crop. Prod. 32, 41-47.

Kumar N, Vijay Anand K G, Reddy M P (2011a). Plant regeneration of non-toxic *Jatropha curcas*-impacts of plant growth regulators, source and type of explants. J. Plant Biochem. Biotechnol. 20: 125-133.

Kumar N, Vijay Anand K G, Reddy M P (2011b). In vitro regeneration from petiole explants of non-toxic *Jatropha curcas*. Industrial Crops and Products. 33:146-151

Li, M. R., Li, H. Q., Jiang, H. W., 2008. Establishment of an *Agrobacterium*-mediated cotyledon disc transformation method for *Jatropha curcas*. Plant Cell Tiss. Organ Cult. 92, 173-181.

Misra P, Gupta N, Toppo D D, Pandey V, Mishra M K, Tuli R (2010) Establishment of long-term proliferating shoot cultures of elite *Jatropha curcas* L. by controlling endophytic bacterial contamination. Plant Cell Tissue Organ Cult 100:189-197.

Murashige, T. and F. Skoog, 1962. A revised medium for rapid growth and bioassays with tobacco tissue cultures. Physiol. Plant., 15: 473-497.

Openshaw, K., 2000. A review of *Jatropha curcas*: an oil plant of unfulfilled promise. Biomass & Bioenergy 19: 1-15.

Pant K. S., Khosla V., Kumar D., Gairola S. (2006) Seed oil content variation in *Jatropha curcas* L. in different altitudinal ranges and site conditions in H.P. India. Lyonia, 11, 31-34.

Preece J E, and Imel M R (1991). Plant regeneration from leaf explants of *Rhododendron* P.J.M. Hybrids. Sci. Hortic. 48: 159-170.

Rajore, S., and Batra, A., 2005. Efficient plant regeneration via shoot tip explant in *Jatropha curcas* L. J. Plant Biochem. Biotech. 14, 73-75.

Sahoo N, Thirunavoukkarasu M, Behera P R, Satpathy G B (2011) Direct shoot organogenesis from hypocotyl explants of *Jatropha curcas* L. an important bioenergy feedstock. GCB Bioenergy 4:2 234-238.

Sharma., S, Kumar., N, Reddy., M (2011). Regeneration in *Jatropha curcas*: Factors affecting the efficiency of in vitro regeneration. Ind. Crops Prod. doi:10.1016/j.indcrop.2011.02.017.

Singh, A., Reddy, M. P., Chikara, J., Singh, S., 2010. A simple regeneration protocol from stem explants of *Jatropha curcas* a biodiesel plant. Ind. Crop Prod. 31, 209-213.

Sujatha M, and Dhingra M (1993). *Rapid plant regeneration from various explants* of. *Jatropha integerrima*. Plant Cell, Tissue and Organ Culture. 35:293-6.

Sujatha M, and Mukta N (1996). Morphogenesis and plant regeneration from tissue cultures of *Jatropha curcas*. Plant Cell Tissue Organ Cult. 44: 135-141.

Sujatha, M., Makkar, H. P. S., Becker, K., 2005. Shoot bud proliferation from axillary nodes and leaf sections of non-toxic *Jatropha curcas* L. Plant Growth Regul. 47, 83-90.

Wei, Q., Lu, W. D., Loao, Y., Pan, S. L., Xu, Y., Tang, L., Fang, C., 2004. Plant regeneration from epicotyl explants of *Jatropha curcas*. J. Plant Physiol. Mol. Biol. 30, 475-478.

What is claimed is:

1. A method of regenerating *Jatropha* via organogenesis comprising the steps:
    (a) culturing a *Jatropha* explant on a solid shoot bud induction medium to induce the formation of shoot buds, wherein the *Jatropha* explant is a thin section of a petiole, pedicle, peduncle or rachis explant or is a callus tissue from said petiole, pedicle, peduncle or rachis explant, wherein the shoot bud induction medium comprises MS basal salts, B5 vitamins, indole-3-butyric acid (IBA), thidiazuron (TDZ), 6-benzylaminopurine (BA), silver thiosulfate (STS) and casein hydrolysate;
    (b) culturing the shoot buds on a solid shoot bud proliferation and development medium to proliferate and develop the shoot buds, wherein the shoot bud proliferation and development comprises MS basal salts, B5 vitamins, IBA, TDZ, BA, zeatin (Zn), adenine sulfate (AdSO$_4$) and casein hydrolysate;
    (c) culturing a shoot bud clump derived from the developed shoot buds on a solid shoot elongation medium to elongate shoots, wherein the shoot elongation medium comprises MS basal salts, B5 vitamins, BA, kinitin (Kn), gibberellic acid (GA$_3$), adenine sulfate (AdSO$_4$) and casein hydrolysate;
    (d) culturing elongated shoots separated from the shoot bud clump on a solid shoot maturation medium to mature the shoots, wherein the shoot maturation medium comprises MS basal salts, B5 vitamins, IBA, Kn, GA$_3$, adenine sulfate (AdSO$_4$) and casein hydrolysate; and
    (e) dipping the mature shoots in a liquid growth regulator solution and transferring the dipped shoots to soil for growth of *Jatropha* plants, wherein the liquid growth regulator solution comprises MS basal salts, B5 vitamins and IBA.

2. The method of claim 1 which further comprises the following step before step (a):
    culturing thin sections of the explant on a solid callus induction medium to induce organogenic callus tissue, wherein the solid callus induction medium comprises MS basal salts, B5 vitamins, IBA, 2,4-dichlorophenoxyacetic acid (2,4-D), TDZ, BA, and proline.

3. The method of claim 2, wherein the solid callus induction medium comprises:
    IBA in an amount from about 0.05 µM to about 4.90 µM;
    2,4-D in an amount from about 0.05 µM to about 4.53 µM;
    TDZ in an amount from about 0.05 µM to about 2.27 µM;
    BA in an amount from about 0.04 µM to about 4.44 µM; and
    proline in an amount from about 10 mg/l to about 500 mg/l.

4. The method of claim 3, wherein the solid callus induction medium comprises:
    IBA in an amount of about 0.49 µM;
    2,4-D in an amount of about 0.45 µM;
    TDZ in an amount of about 0.45 µM;
    BA in an amount of about 0.66 µM; and
    proline in an amount of about 100 mg/l.

5. The method claim 1, wherein the media comprise:
    shoot bud induction medium comprises:
        IBA in an amount from about 0.05 µM to about 4.90 µM;
        TDZ in an amount from about 0.05 µM to about 2.27 µM;
        BA in an amount of from about 0.02 µM to about 4.44 µM;
        STS in an amount from about 0.10 µM to about 20 µM; and
        casein hydrolysate in an amount from about 5 mg/l to about 200 mg/l;
    shoot bud proliferation and development medium comprises:
        IBA in an amount from about 0.05 µM to about 4.90 µM;
        TDZ in an amount from about 0.01 µM to about 2.27 µM;
        BA in an amount of from about 0.04 µM to about 4.44 µM;
        Zn in an amount of from about 0.05 µM to about 4.56 µM;
        AdSO$_4$ in an amount from about 5.43 µM to about 271.5 µM; and
        casein hydrolysate in an amount from about 5 mg/l to about 200 mg/l;
    shoot bud elongation medium comprises:
        BA in an amount from about 0.04 µM to about 4.44 µM;
        Kn in an amount from about 0.05 µM to about 4.65 µM;
        GA$_3$ in an amount from about 0.03 µM to about 2.89 µM;
        AdSO$_4$ in an amount from about 5.43 µM to about 271.5 µM; and
        casein hydrolysate in an amount from about 5 mg/l to about 200 mg/l;
    shoot maturation medium comprises:
        IBA in an amount from about 0.05 µM to about 4.90 µM;

Kn in an amount from about 0.05 µM to about 4.65 µM;
GA$_3$ in an amount from about 0.03 µM to about 2.89 µM;
AdSO$_4$ in an amount from about 5.43 µM to about 271.5 µM; and
casein hydrolysate in an amount from about 5 mg/l to about 200 mg/l; and
liquid growth regulator solution comprises:
IBA in an amount from about 4.90 µM to about 245.0 µM.

6. The method of claim 5, wherein the media comprise:
shoot bud induction medium comprises:
IBA in an amount of about 0.98 µM;
TDZ in an amount of about 0.45 µM;
BA in an amount of about 0.22 µM;
STS in an amount of about 4.0 µM; and
casein hydrolysate in an amount of about 100 mg/l;
shoot bud proliferation and development medium comprises:
IBA in an amount of about 0.49 µM;
TDZ in an amount of about 0.23 µM;
BA in an amount of about 0.44 µM;
Zn in an amount of about 0.92 µM;
AdSO$_4$ in an amount of about 135.75 µM; and
casein hydrolysate in an amount of about 100 mg/l;
shoot bud elongation medium comprises:
BA in an amount of about 0.66 µM;
Kn in an amount of about 1.17 µM;
GA$_3$ in an amount of about 0.73 µM;
AdSO$_4$ in an amount of about 135.75 µM; and
casein hydrolysate in an amount of about 100 mg/l;
shoot maturation medium comprises:
IBA in an amount of about 0.49 µM;
Kn in an amount of about 1.17 µM;
GA$_3$ in an amount of about 0.73 µM;
AdSO$_4$ in an amount of about 135.75 µM; and
casein hydrolysate in an amount of about 100 mg/l; and
liquid growth regulator solution comprises:
IBA in an amount of about 49.0 µM.

7. The method of claim 1, wherein each medium further comprises from about 0.5% to about 10% sucrose and from about 0.5% to about 1.0% agar.

8. The method of claim 7, wherein each medium comprises about 3% sucrose and about 0.8% agar.

9. The method of claim 1, wherein each culturing step is carried out at 25±2° C.

10. The method of claim 1, wherein each culturing step is carried out with at a 16 hr light/8 hr dark photoperiod condition at a light intensity of 150 µEm$^{-2}$s$^{-1}$.

11. The method of claim 1, wherein the culturing is carried out for the following times:
about 2 weeks to about 4 weeks for callus induction;
about 2 weeks to about 5 weeks for shoot bud induction when the explant is a thin section of a petiole, pedicle, peduncle or rachis explant or about 4 weeks to about 8 weeks for shoot bud induction when the explant is callus tissue from said petiole, pedicle, peduncle or rachis explant;
about 2 weeks to about 4 weeks for shoot proliferation and development;
about 2 weeks to about 4 weeks for shoot elongation; and
about 2 weeks to about 6 weeks for shoot maturation.

12. The method of claim 11, wherein the culturing is carried out for the following times:
about 3 weeks for callus induction;
about 4 weeks for shoot bud induction when the explant is a thin section of a petiole, pedicle, peduncle or rachis explant or about 7 weeks for shoot bud induction when the explant is callus tissue from said petiole, pedicle, peduncle or rachis explant;
about 3 weeks for shoot proliferation and development;
about 3 weeks for shoot elongation; and
about 3 weeks for shoot maturation.

\* \* \* \* \*